(12) United States Patent
Nazemi

(10) Patent No.: US 11,633,298 B2
(45) Date of Patent: Apr. 25, 2023

(54) PORTABLE URINAL DEVICE

(71) Applicant: Patrick Nazemi, Encino, CA (US)

(72) Inventor: Patrick Nazemi, Encino, CA (US)

( * ) Notice: Subject to any disclaimer, the term of this patent is extended or adjusted under 35 U.S.C. 154(b) by 0 days.

(21) Appl. No.: 17/166,772

(22) Filed: Feb. 3, 2021

(65) Prior Publication Data

US 2021/0267787 A1 Sep. 2, 2021

Related U.S. Application Data

(60) Provisional application No. 62/982,400, filed on Feb. 27, 2020.

(51) Int. Cl.
*A61F 5/455* (2006.01)
*A61F 5/453* (2006.01)
*A61F 5/44* (2006.01)

(52) U.S. Cl.
CPC ............ *A61F 5/455* (2013.01); *A61F 5/4401* (2013.01); *A61F 5/4408* (2013.01); *A61F 5/453* (2013.01); *A61M 2205/273* (2013.01)

(58) Field of Classification Search
CPC ...... A61F 5/455; A61F 5/4401; A61F 5/4408; A61F 5/453; A61M 2205/273; A61M 1/71; A61M 1/80; A61M 1/87; A61M 2202/0496; A61M 39/0613; A61M 2039/0673; A61M 2039/062; A61M 39/06
See application file for complete search history.

(56) References Cited

U.S. PATENT DOCUMENTS

| | | | | |
|---|---|---|---|---|
| 1,039,887 | A * | 10/1912 | Bauroth | B21D 51/44 72/353.4 |
| 3,336,926 | A * | 8/1967 | Gresham | A61F 5/453 D24/112 |
| 5,002,541 | A * | 3/1991 | Conkling | A61F 5/44 604/324 |
| 6,740,066 | B2 * | 5/2004 | Wolff | A61F 5/451 604/323 |
| 7,186,245 | B1 * | 3/2007 | Cheng | A61F 5/44 604/350 |
| 7,749,205 | B2 * | 7/2010 | Tazoe | A61F 5/451 604/320 |
| 7,993,311 | B2 * | 8/2011 | Finger | A61G 9/00 604/350 |
| 8,608,717 | B2 * | 12/2013 | Tung | A61F 5/453 604/347 |
| 10,390,989 | B2 * | 8/2019 | Sanchez | A61F 5/453 |
| 10,517,538 | B2 * | 12/2019 | Burnett | A61B 5/0245 |
| 2004/0230181 | A1 * | 11/2004 | Cawood | A61F 5/453 604/544 |
| 2004/0243075 | A1 * | 12/2004 | Harvie | A61F 5/451 604/355 |
| 2006/0235359 | A1 | 10/2006 | Marland | |

(Continued)

FOREIGN PATENT DOCUMENTS

WO WO-2016126555 A1 * 8/2016 ............ A61B 50/33

*Primary Examiner* — Susan S Su
*Assistant Examiner* — Eric Rassavong
(74) *Attorney, Agent, or Firm* — Kelly & Kelley, LLP

(57) ABSTRACT

A portable urinal device includes a base forming a liquid receptacle. Tubing extends from the base to a head member which can be positioned onto genitalia for urination. Suction is provided via a pump or vacuum device to suction urine from the head into the base receptacle.

39 Claims, 6 Drawing Sheets

(56) References Cited

U.S. PATENT DOCUMENTS

| | | | |
|---|---|---|---|
| 2010/0094173 A1* | 4/2010 | Denton | A61M 1/7415 |
| | | | 604/323 |
| 2011/0178484 A1 | 7/2011 | Zivley | |
| 2016/0374848 A1* | 12/2016 | Sanchez | A61F 5/453 |
| | | | 604/319 |
| 2017/0281399 A1* | 10/2017 | VanMiddendorp | A61F 5/455 |

* cited by examiner

PORTABLE URINAL DEVICE

RELATED APPLICATIONS

This application claims the benefit of U.S. Provisional Application No. 62/982,400, filed on Feb. 27, 2020.

BACKGROUND OF THE INVENTION

The present invention is generally related to urinals. More particularly, the present invention is related to a portable urinal which provides suction for urinating while sitting, standing or lying down.

A frequent need to get up and go to the bathroom to urinate at night is called nocturia. It is a common cause of sleep loss, especially among older adults. Most people without nocturia can sleep for six to eight hours without having to urinate.

Nocturia can be caused during pregnancy or those with a variety of medical conditions, including urological infection, enlarged prostate, or disorders affecting sphincter control. Diabetes, heart failure, liver failure, and diuretic medications are also associated with nocturia. It is estimated that nearly two-thirds of adults between the ages of fifty-five and eighty-four have systems of nocturia or frequent nighttime urination at least occasionally, if not nightly. Sometimes, nocturia may simply be the result of drinking too many fluids, especially caffeine, before going to bed.

The urge to urinate during the night requires one to exit his or her bed, and walk to the bathroom. Typically, the individual needs to turn on the lights in the bedroom and/or the bathroom. The act of getting out of bed, walking and turning on the light can provide stimulation to awake the individual, sometimes resulting in the individual having difficulty returning to sleep immediately.

Even awaking once or twice during the night to urinate can adversely impact an individual's sleep patterns and cause tiredness and daytime fatigue, adversely impacting the individual's ability to effectively perform his or her functions throughout the day. Getting up to urinate two or more events per night may be associated with daytime tiredness. People with severe nocturia may get up five or six times during the night to go to the bathroom, creating extreme daytime tiredness and affecting the person's ability to function throughout the day.

Portable, handheld urinals are known. These urinals may be comprised of a container which can be held in one's hand and which has a sufficiently large opening in which to urinate. Such portable urinals are commonly used in a vehicle during long drives or the like. They are very simple in nature and their use has drawbacks. The opening or passage to the portable urinal may accommodate male genitalia, but not accommodate female genitalia. Spills may also occur either during use of the urinal or afterwards.

Accordingly, there is a continuing need for an improved portable urinal device. Such a urinal device should overcome the drawbacks associated with conventional portable urinals, including reducing the possibility of spillage. Moreover, such an improved urinal device should be particularly suited for use during the night, or for those who may be confined to a bed or the like. The present invention fulfills these needs, and provides other related advantages.

SUMMARY OF THE INVENTION

The present invention is directed relates to a portable urinal device which provides suction for urinating so as to reduce the chances of spillage and be able to be used while sitting, standing or lying down.

The portable urinal device of the present invention generally comprises a base comprising a urine receptacle. A hollow tube extends from the base and has a first end in fluid communication with the urine receptacle. The tube may be automatically retractable from and to the base.

A head member is attached to a second end of the hollow tube. The head member may be removably attached to the second end of the tube. The head may be comprised of a soft plastic or rubber material. The head may be disposable, or a disposable liner may be placed over the head. The head may be inflatable.

The head member is configured to be placed over a user's genitalia. The head may have a male configuration adapted for placement over an end of a penis. Alternatively, the head may have a female configuration for placement over a vagina.

A pump creates a negative pressure in the hollow tube for suctioning urine from the user's genitalia through the hollow tube and into the urine receptacle. A switch activates the pump. The switch may be automatically actuated when the tube is extended from the base. The pump may be automatically turned off after a predetermined period of time. Alternatively, the pump may be turned off upon the return of the tube to the base. The pump may be selectively reversible so as to create a positive pressure to evacuate fluid from the urine receptacle.

A wipe or toilet paper may be attached to the base so that the user can conveniently clean himself or herself and/or the device as needed.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

As shown in the accompanying drawings, for purposes of illustration, the present invention resides in a urinal device, generally referred to by the reference 100. The urinal device 100 is portable and is particularly adapted for use by those having the urge to urinate during the night, who are confined to a bed, or in other instances when a convenient and portable urinal is desirable.

Figure 1:
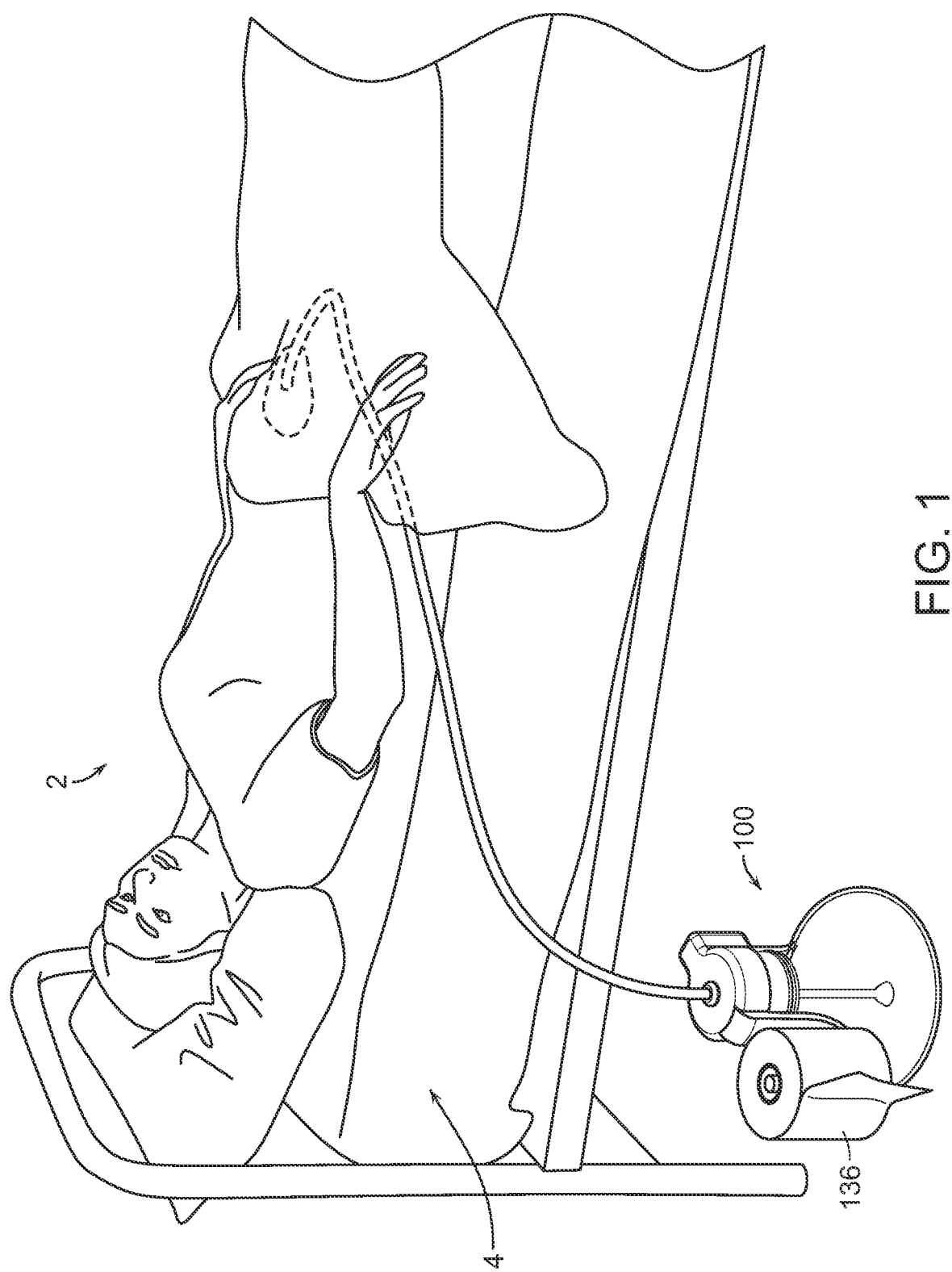
FIG. 1 is an environmental perspective view of a user in bed and utilizing a portable urinal device embodying the present invention.
Figure 2:
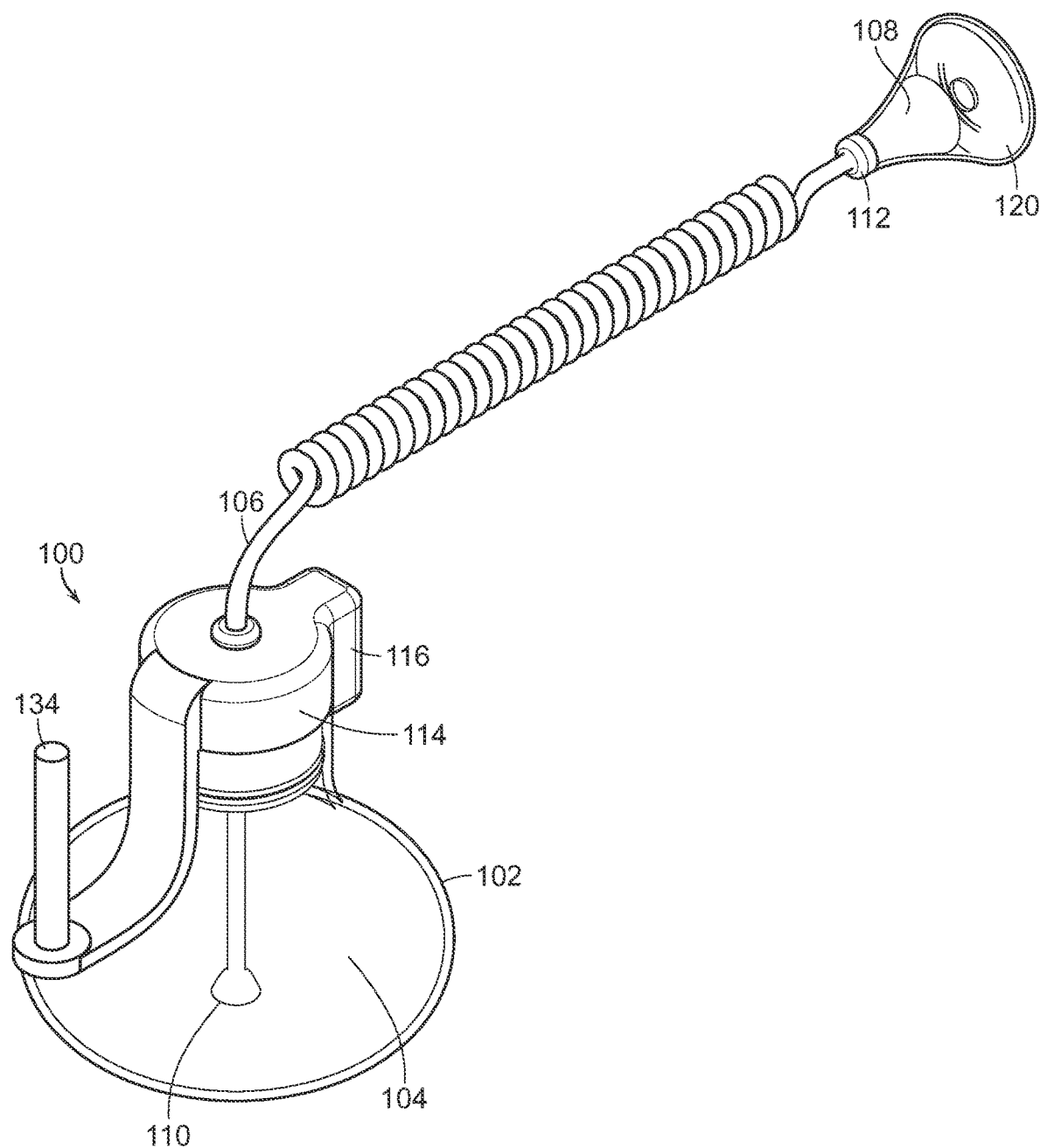
FIG. 2 is a side perspective view of a portable urinal device embodying the present invention.
Figure 3:
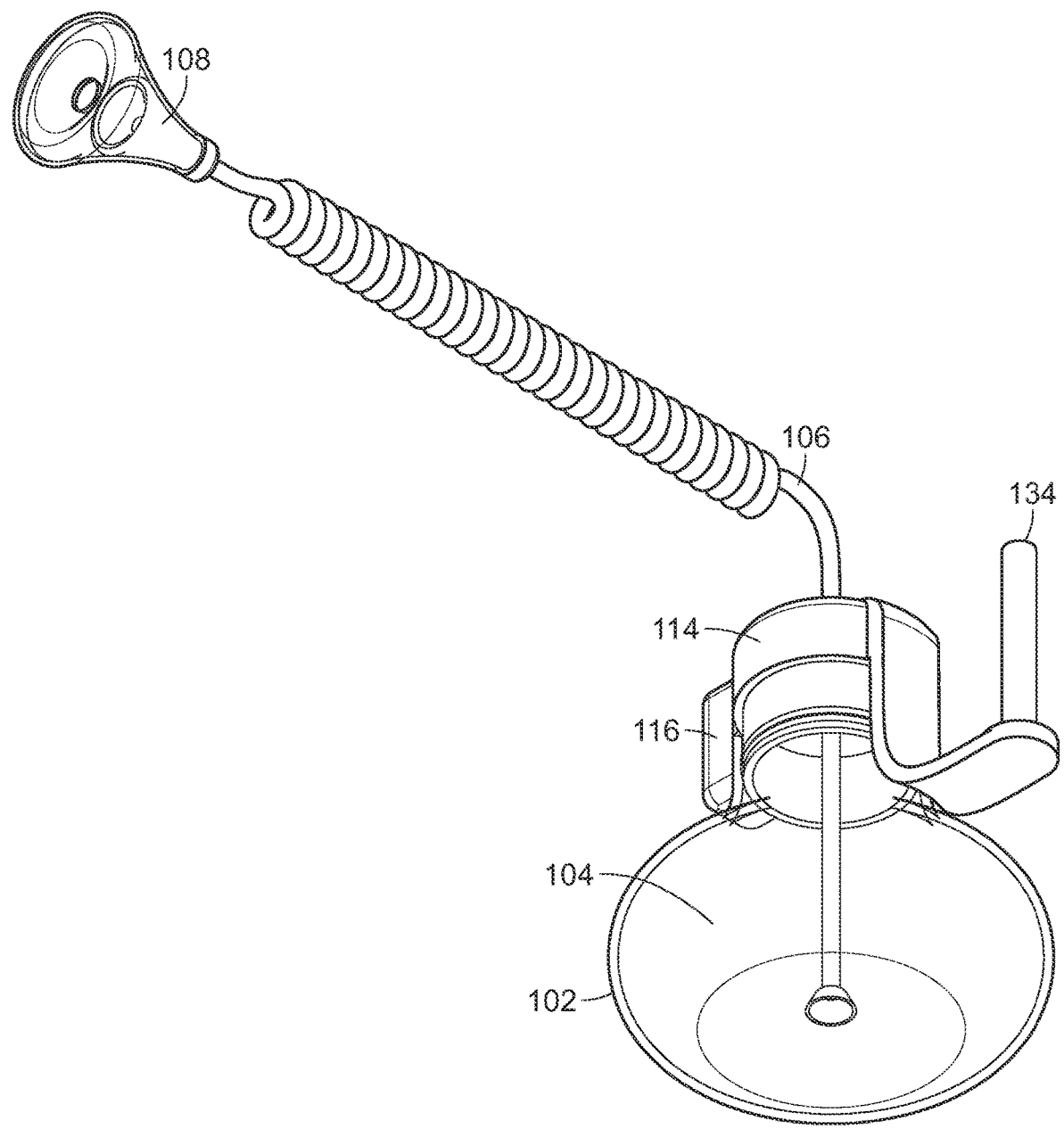
FIG. 3 is a lower and generally opposite perspective view of the urinal device of FIG. 2.
Figure 4:
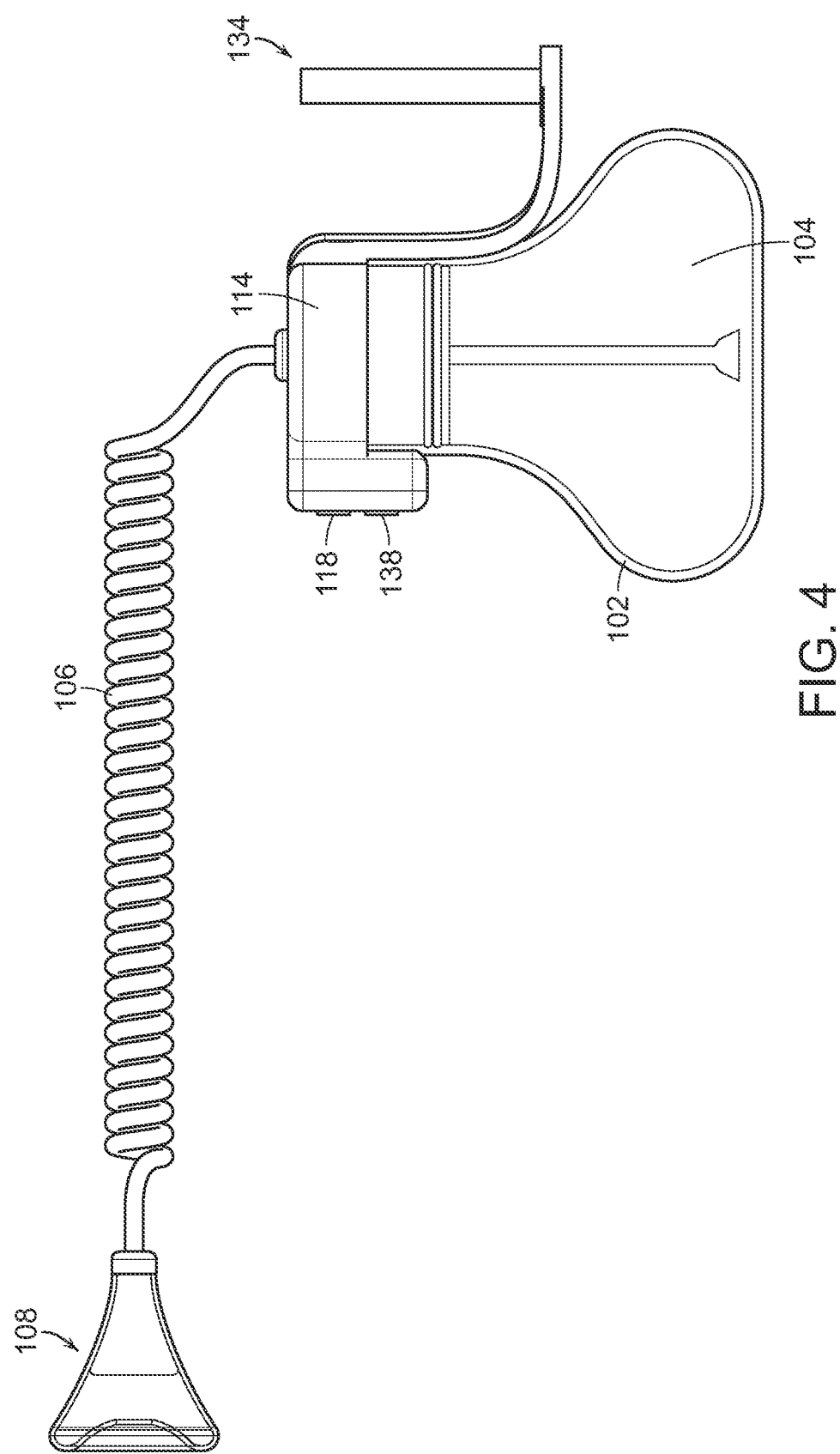
FIG. 4 is a side view of the portable urinal device.
Figure 5:
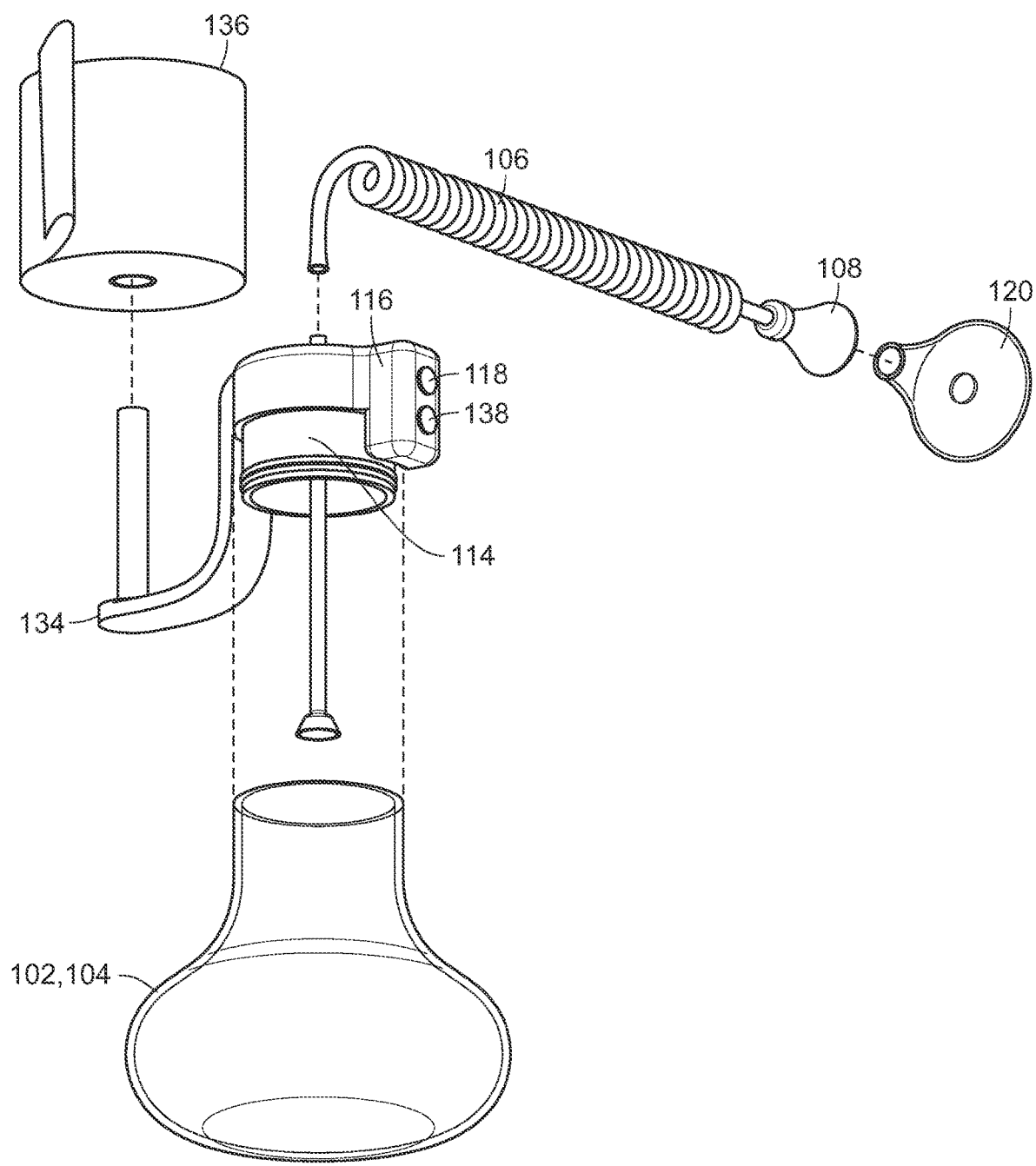
FIG. 5 is an exploded perspective view, illustrating various components of the portable urinal device.

With reference to FIG. 1, the portable urinal device 100 of the present invention may be used by a user when standing, sitting or lying down. It is particularly suited, however, for those individuals who are sitting or lying down, such as a user 2 lying in a bed 4, such as during the night when the user 2 is sleeping. Instead of having to get out of the bed and walk to the bathroom, the user 2 may instead either sit up on the side of the bed and use the urine device 100, or even remain in the bed and use the urine device 100, as will be more fully explained herein. Thus, the user can avoid the stimulations of getting out of bed, walking and turning on lights and thus will be able to go back to sleep more quickly, resulting in a better night's sleep. The present invention could also be used in other circumstances, such as for users who are confined to a bed, wheelchair or the like. The present invention could also be utilized by those who are driving long distances where a restroom is unavailable or the driver desires to avoid stopping.

With reference now to FIGS. 2-5, the urinal device 100 includes a base 102 which can be placed on a bed stand, floor, tabletop or any other surface next to the user. The base 102 comprises a urine receptacle. The base 102 and urine receptacle 104 may be separate components attached or associated with one another, or the base 102 may be at least partially hollow so as to form the urine receptacle 104 therein, as illustrated.

A hollow tube 106 extends from the base 102 to a head member 108. A first end 110 of the tube 106 is in fluid communication with the urine receptacle 104, such as being disposed therein, as illustrated. A second open end 112 of the tube 106 is attached to the head member 108. The tube 106 may have elastic or spring-like characteristics, so as to automatically retract after use. Such characteristics can also enable the tube 106 to be extended from the base to the individual's genitals while standing near the base, sitting near the base, such as on one's bed, or lying in bed. It will be understood that the tube 106 may be a single tube, or multi-segmented and interconnected to one another, so as to provide a tube of greater length which may be desirable depending upon the distance between the urine device 100 and the user, such as when the device 100 is placed on a table, bedstand or the like which is some distance from the user when lying in bed. As illustrated, the tube 106 may be coiled, or have other elastic or spring-like characteristics, so as to be extendable and automatically contactable after use. The tube 106 may also be extendable and retractable into and out of a cover housing 114.

A pump 116, such as a battery-powered, or DC or AC powered pump, is operably associated with the device 100, such that suction is provided through the head 108 and tube 106 such that as urine enters the head member 108, it is suctioned into the reservoir 104. The suction facilitates the removal of the urine from the individual to the receptacle 104, and reduces or even eliminates the possibility of spillage and the like.

A switch 116 may be used to activate the pump 114. The switch may be turned from off to on automatically when the head member 108 and/or the tube 106 is/are pulled towards the user away from the device 110, and automatically powered off when returned to its location on the base 102. For example, extending the tube 104 may activate a sensor, such as a motion sensor, timer or the like such that the motor 108 is activated and suction is applied to the device 100.

In another alternative, the switch or sensor is associated with the head member 108 so as to be activated when the user begins to use the device 100, presses a switch associated with the head member 108, or even compresses the head member 108 so as to activate the pump 114 and suction. The switch 116 may be a simple on and off switch, or may activate a timer, after a predetermined period of time the pump 114 will automatically cease operation. The switch or timer may also be activated when the tube 106 is extended, and deactivated when the tube 106 is retracted back into its original resting place.

The head member 108 may be generally funnel-shaped, as illustrated in the various drawings. Preferably, the head member 108 is of a sufficiently large size so as to be placed over the individual's genitals to enable the individual to urinate into the head 108, and dispense the urine through the head 108 to the tube 106 and into the urine receptacle 104.

The head 108 may be comprised of a soft material, such as rubber, elastic or the like. The head 108 may have a cover 120 formed integrally therewith, and permanently attached thereto, or removably attached thereto. The head 108 may be removably attached to the second end 112 of the tube 106. The head 108 may be formed of a more rigid material, whereas the cover 120 is comprised of a softer material. The cover 120 and/or head 108 may be squeezable or compressible, so as to more closely conform to the individual's genitalia to prevent leakage. The head 108 may be disposable for one-time use or it may have a disposable cover that is placed on the head 108 for one-time use.

Figure 6:
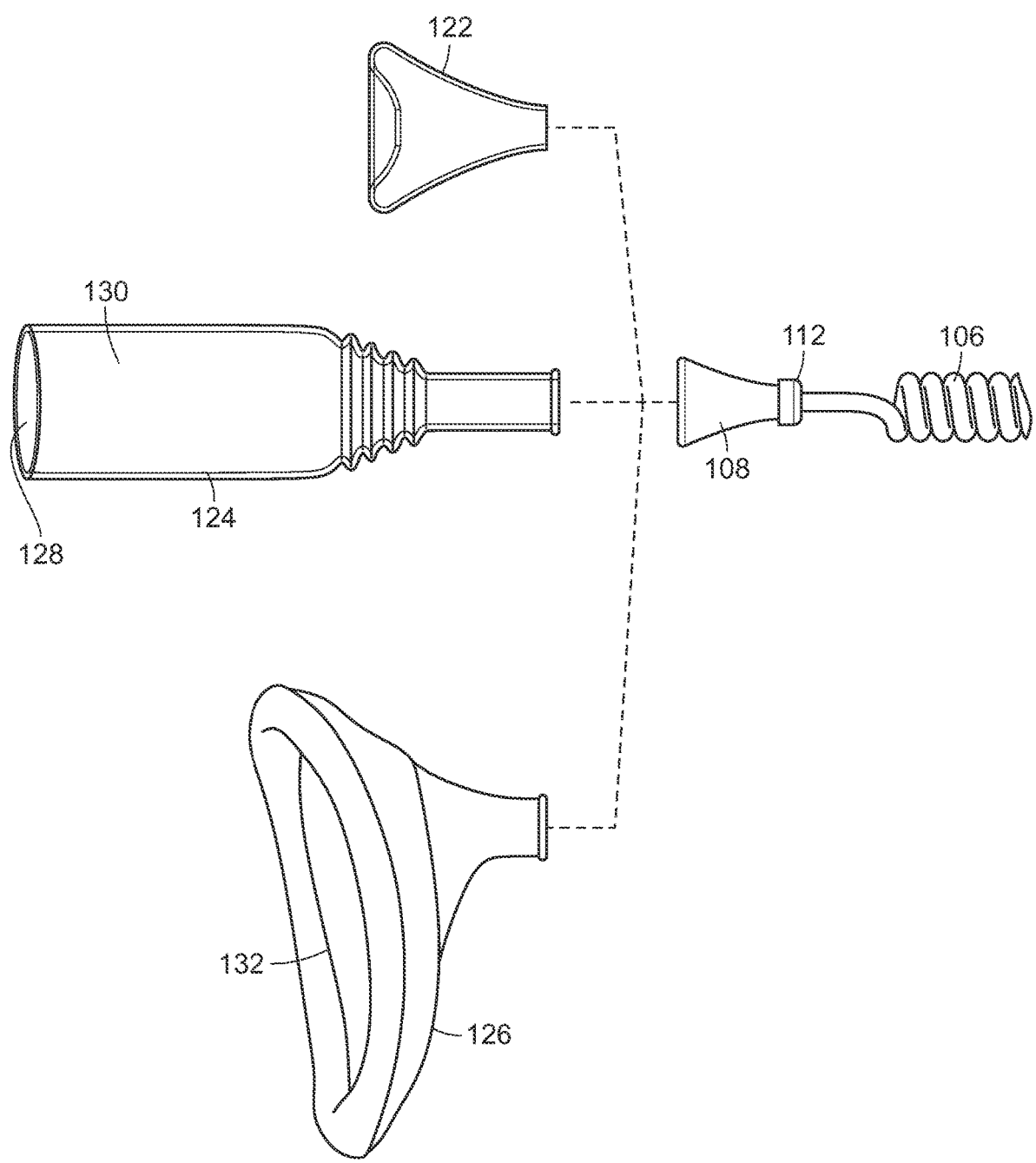
FIG. 6 is an exploded side view of alternate head members or covers used in accordance with the present invention.

As illustrated in FIG. 6, the head member 108 can be of a variety of configurations. The configurations can be configured to be used by male genitalia, a female genitalia, and thus be of a different configuration, size, etc. As shown in FIG. 6, either a cover may be attached to the head 108, which may be disposable or usable, and which may be of a configuration and size so as to accommodate and be adapted for use for different genitalia. For example, a cover or head 122 may either be attached to head member 108 or attached to the second end 112 of the tube 106 and have a universal configuration. Cover or head 124 is of a male genitalia configuration, and cover or head 126 is of a female genitalia configuration. The male cover or head 124 has an opening 128 and chamber 130 for the insertion of a penis therein. Whereas the female cover or head 126 has an opening of a configuration to form around a vagina. As mentioned above, either the cover or head may be compressible so as to be formed around the genitalia, such as to prevent leakage. The cover or head may also be inflatable to achieve the same purposes.

As mentioned above, the urinal device 100 of the present invention is particularly suited to aid a person who is sleeping and has the urge to urinate, without having to get up to use the restroom. It may also be used for immobile patients, paraplegics which must lie down in a bed or are confined to a wheelchair or are otherwise immobilized. It could also be used in other circumstances, such as when on long drives or the like.

When ready to urinate, the user pulls the head member 108 from its resting position or socket, towards his or her genitalia. The suction either begins automatically, or the head member 108 is squeezed, or a switch 118 is manually actuated or the like in order to power motor 116 and begin the suction. The device 100 will then suction all of the liquid as it comes into the head member 108 and deposits the urine into the urine receptacle 104. Once finished, the individual places the head member 108 back on the base or otherwise on its resting position, after which the suction will either stop automatically due to a timer, sensor, or the like or the user manually switching the device 100 off.

The device 100 may also include a toilet paper, or wipe, holder or retainer 134. This may be associated with, attached to, or extend from the base 102 and allow the individual to selectively extract a desired amount of toilet paper 136 or a wipe for cleaning his or her hands and/or genitals after using the device 100. As illustrated in the various figures, the retainer 134 comprises a rod upon which a roll of toilet paper 136 may be placed. The bracket and rod comprising the retainer 134 enables the toilet paper roll 136 to be rotated as toilet paper is removed from the roll. However, the retainer 134 can take other configurations and may be instead configured to hold and dispense wipes or the like.

After use, such as in the morning after a night of sleeping, urine can be removed from the urine receptacle 104. This may be done by tilting the unit 100 so as to empty the urine from the receptacle 104. This might require the removal of the housing cover 114 from the base 102 and/or receptacle 104. Alternatively, the receptacle 104 may be detachably connected to the base 102 and thus emptied. The invention also anticipates that a reverse vacuum action may be provided, such as the pump being operated in reverse, such as actuating switch 138, so as to reverse the flow of fluid from the urine receptacle 104, through the tube 106 and out the head 108 or second end 112 of the tube for disposal. Fresh water or a cleaning solution may be passed through the head 108, tube 106 and various components into the receptacle 104 and then emptied from the device 100, as described above.

Use of the device 100 of the present invention enables an individual to avoid having to get out of bed, walk to the bathroom, and turn on and off lights, which can take time and disrupt the user's sleep. Use of the device 100 also enables caretakers to more easily assist a patient or loved one in urinating.

In addition to the functions and benefits described above, the head member 108, additionally or alternatively, may serve to sexually stimulate the genitalia of the user. The suction generated by the device 100 and the configuration, material, placement and/or manipulation of the head 108 can perform such objectives. This may be, for example, by creating a specially-configured head 108 to achieve such sexual stimulation objective either in addition to, or alternatively, to the urine suction described above.

Although several embodiments have been described in detail for purposes of illustration, various modifications may be made without departing from the scope and spirit of the invention. Accordingly, the invention is not to be limited, except as by the appended claims.

What is claimed is:

1. A portable urinal device, comprising:
   a base comprising a urine receptacle;
   a hollow tube extending from the base and having a first end in fluid communication with the urine receptacle;
   a head member attached to a second end of the hollow tube, the head member configured to be placed over a user's genitalia; and
   a pump that creates a negative pressure in the hollow tube for suctioning urine from the user's genitalia through the hollow tube and into the urine receptacle;
   wherein the pump is selectively reversible so as to create a positive pressure to evacuate fluid from the urine receptacle.

2. The device of claim 1, wherein the tube is automatically retractable from and to the base.

3. The device of claim 1, wherein the head member is comprised of a soft plastic or rubber material.

4. The device of claim 1, wherein the head member is removably attached to the tube.

5. The device of claim 1, wherein the head member has a male configuration adapted for placement over an end of a penis or a female configuration for placement over a vagina.

6. The device of claim 1, wherein the head member is disposable or a disposable liner is placed over the head member.

7. The device of claim 1, wherein the head member is inflatable.

8. The device of claim 1, including a switch for activating the pump.

9. The device of claim 8, wherein the switch is automatically actuated when the tube is extended from the base.

10. The device of claim 9, wherein the pump automatically powers off after a predetermined period of time or upon the return of the tube to the base.

11. The device of claim 1, including a wipe or toilet paper attached to the base.

12. A portable urinal device, comprising:
    a base comprising a urine receptacle;
    a hollow tube extending from the base and having a first end in fluid communication with the urine receptacle;
    a head member removably attached to a second end of the hollow tube, the head member having either a male configuration adapted to be placed over a male user's genitalia or a female configuration adapted to be placed over a female user's genitalia; and
    a pump that creates a negative pressure in the hollow tube for suctioning urine from the user's genitalia through the hollow tube and into the urine receptacle;
    wherein the pump is automatically actuated when the head member and/or tube is extended from the base.

13. The device of claim 12, wherein the tube is automatically retractable from and to the base.

14. The device of claim 12, wherein the head member is comprised of a soft plastic or rubber material.

15. The device of claim 12, wherein the head member is disposable or a disposable liner is placed over the head member.

16. The device of claim 12, wherein the head member is inflatable.

17. The device of claim 12, including a switch for activating the pump.

18. The device of claim 12, wherein the pump automatically powers off after a predetermined period of time or upon the return of the tube to the base.

19. The device of claim 12, including a holder for wipes or toilet paper attached to the base.

20. The device of claim 12 wherein the base defines a generally planar bottom portion configured to be placed on a table or bed stand and having a urine receptacle extending upwardly from the bottom portion.

21. A portable urinal device, comprising:
    a base defining a solid generally planar bottom portion configured to be placed on a table or bed stand and having a urine receptacle extending upwardly from the bottom portion;
    a hollow tube extending from the base and having a first end in fluid communication with the urine receptacle;
    a head member removably attached to a second end of the hollow tube, the head member having either a male configuration adapted to be placed over a male user's genitalia or a female configuration adapted to be placed over a female user's genitalia; and
    a pump that creates a negative pressure in the hollow tube for suctioning urine from the user's genitalia through the head member and hollow tube and into the urine receptacle;
    wherein the pump is automatically actuated when the head member and/or tube is extended from the base and automatically powered off after a predetermined period of time or upon the return of the head member or tube to the base.

22. The device of claim 21, wherein the tube is automatically retractable from and to the base.

23. The device of claim 21, wherein the head member is disposable or a disposable liner is placed over the head member.

24. The device of claim 21, wherein the head member is inflatable.

25. The device of claim 21, wherein the pump automatically powers off after a predetermined period of time.

26. The device of claim 21, including a holder for wipes or toilet paper attached to the base.

27. A portable urinal device, comprising:
   a base comprising a urine receptacle extending upwardly from a bottom portion thereof;
   a hollow tube extending from the base and having a first end in fluid communication with the urine receptacle;
   a reusable head member removably attached to a second end of the hollow tube, the head member having a configuration adapted to be placed over a male user's genitalia and have at least a portion of a penis inserted therein; and
   a pump that creates a negative pressure in the hollow tube for suctioning urine from the user's genitalia through the head member and hollow tube and into the urine receptacle;
   wherein the pump is automatically actuated when the head member and/or tube is extended from the base and automatically powered off after a predetermined period of time or upon the return of the head member or tube to the base.

28. The device of claim 27, wherein the tube is automatically retractable from and to the base.

29. The device of claim 27, including a disposable liner placed over the head member.

30. The device of claim 27, wherein the head member is inflatable.

31. The device of claim 27, wherein the pump automatically powers off after a predetermined period of time.

32. The device of claim 27, including a holder for wipes or toilet paper attached to the base.

33. A portable urinal device, comprising:
   a base defining a generally planar bottom portion and a urine receptacle extending upwardly from the bottom portion;
   a rod extending from the base and comprising a holder upon which a toilet paper roll is disposed;
   a hollow tube extending from the base and having a first end in fluid communication with the urine receptacle;
   a head member removably attached to a second end of the hollow tube, the head member having either a male configuration adapted to be placed over a male user's genitalia or a female configuration adapted to be placed over a female user's genitalia; and
   a pump that creates a negative pressure in the hollow tube for suctioning urine from the user's genitalia through the head member and hollow tube and into the urine receptacle.

34. The device of claim 33, wherein the tube is automatically retractable from and to the base.

35. The device of claim 33, wherein the head member is disposable or a disposable liner is placed over the head member.

36. The device of claim 33, wherein the head member is inflatable.

37. The device of claim 33, wherein the pump is automatically actuated when the head member and/or tube is extended from the base and automatically powered off after a predetermined period of time or upon the return of the head member or tube to the base.

38. The device of claim 33, wherein the pump automatically powers off after a predetermined period of time.

39. A portable urinal device, comprising:
   a base comprising a urine receptacle extending upwardly from a bottom portion thereof;
   a hollow tube extending from the base and having a first end in fluid communication with the urine receptacle;
   a reusable head member removably attached to a second end of the hollow tube, the head member having a configuration adapted to be placed over a male user's genitalia and have at least a portion of a penis inserted therein; and
   a pump that creates a negative pressure in the hollow tube for suctioning urine from the user's genitalia through the head member and hollow tube and into the urine receptacle;
   wherein the head member is inflatable.

* * * * *